United States Patent [19]
Ruppert

[11] Patent Number: 5,129,913
[45] Date of Patent: Jul. 14, 1992

[54] SURGICAL PUNCH APPARATUS

[76] Inventor: Norbert Ruppert, 1501 Lexington Ave., Deland, Fla. 32724

[21] Appl. No.: 592,520

[22] Filed: Oct. 4, 1990

[51] Int. Cl.$^5$ ............................................. A61B 17/32
[52] U.S. Cl. ........................................ 606/184; 606/171; 128/754
[58] Field of Search ............ 606/159, 171, 180, 184, 606/170; 604/22; 128/753-755; 30/263, 240

[56] References Cited

U.S. PATENT DOCUMENTS

| | | | |
|---|---|---|---|
| 1,867,624 | 7/1932 | Hoffman. | |
| 2,433,058 | 12/1947 | Mesaros | 164/33 |
| 2,505,358 | 4/1950 | Gusberg et al. | 128/2 |
| 2,994,321 | 8/1961 | Tischler | 128/2 |
| 3,104,666 | 9/1963 | Hale et al. | 128/305 |
| 3,776,237 | 12/1973 | Hill et al. | 128/305 |
| 3,837,345 | 9/1974 | Matar | 128/305 |
| 4,018,228 | 4/1977 | Goosen | 128/305 |
| 4,712,545 | 12/1987 | Honkanen | 128/305 |
| 4,926,858 | 5/1990 | Gifford et al. | 606/159 |
| 4,979,951 | 12/1990 | Simpson | 606/159 |

*Primary Examiner*—Michael H. Thaler
*Attorney, Agent, or Firm*—James H. Beusse

[57] ABSTRACT

A surgical punch apparatus incorporating a fixed cutter blade and a sliding cutter blade incorporates a drive mechanism which causes the sliding cutter blade to rotate with respect to the fixed cutter blade. Relative rotation effects a slicing action between the blades to facilitate cutting and to enhance longevity of the blade without sharpening.

3 Claims, 2 Drawing Sheets

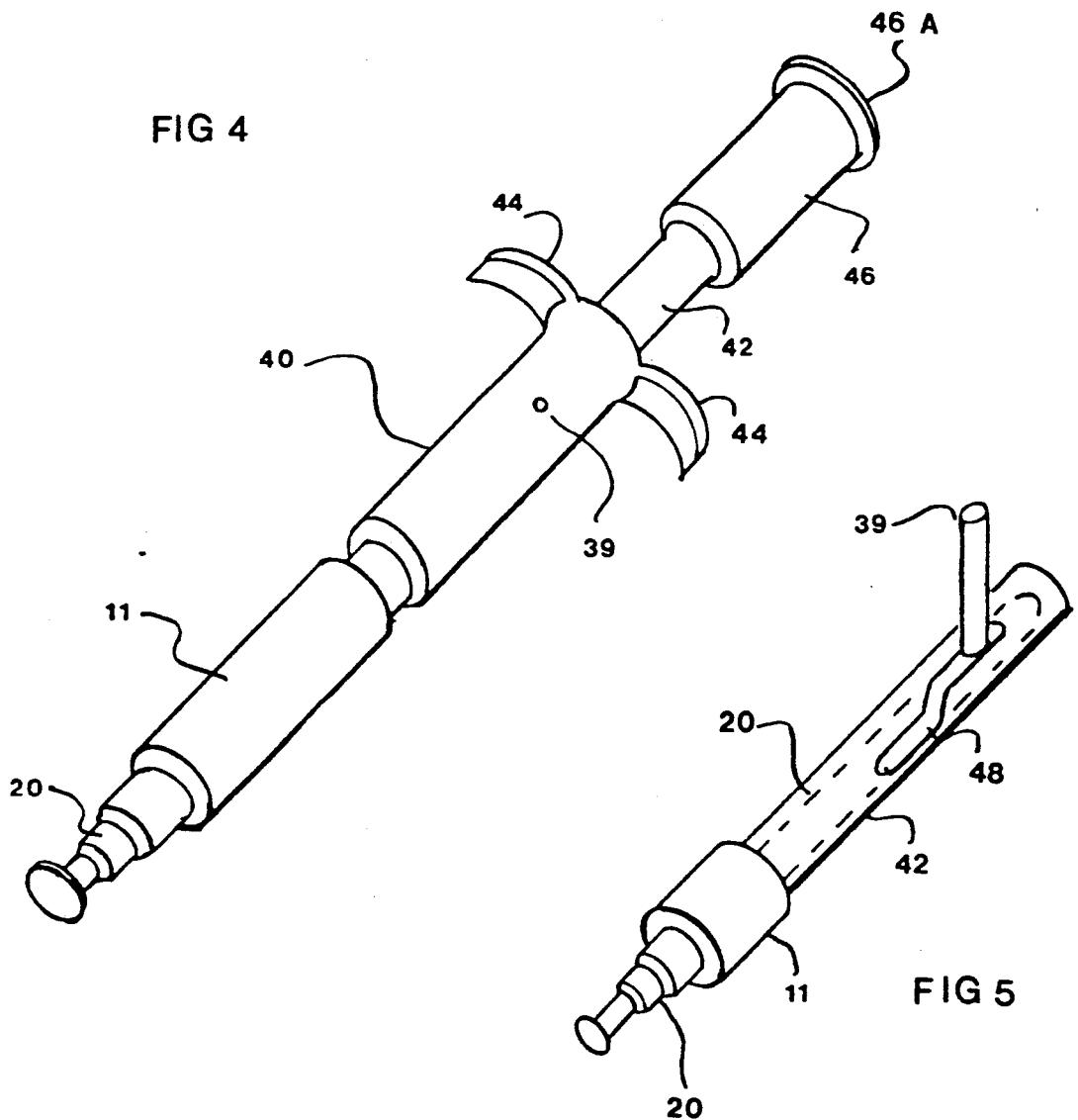

SURGICAL PUNCH APPARATUS

The present invention relates to surgical instruments and, more particularly, to an aorta punch for use in saphenous vein grafts, and the like.

BACKGROUND OF THE INVENTION

In cardiac surgery, saphenous vein grafts are used to bypass diseased areas of the coronary arteries, and the present invention is used in the preparation of an opening in the ascending aorta where the proximal end of the saphenous vein may be anastomosed. Incisions in the aorta can be made with surgical scalpels or scissors or combinations of these with the shape varying from widened slits to triangular. It is also known to use a punch in an attempt to provide an accurate, clean circular opening. The function of such a punch depends on the introduction of a support, or anvil into the aorta or artery through an incision in the arterial wall. Using one hand, the thumb and opposed first and second fingers are approximated to pull a cross-bar which pulls down a tubular cutting device which pushes the aortic wall against an anvil in the lumen. Great pressure has to be exerted in order to accomplish the desired result. Such a system has proved unsatisfactory because of the great pressure required by a blade pushing against an anvil. At least as early as 1975, a surgical punch having a cutting mechanism with a shearing, or scissor-like action was developed and is described in U.S. Pat. No. 4,018,228. This improved punch allows the portion of the shearing punch which is introduced into the vessel lumen to share in the cutting action as a fixed blade which slides into the cutting blade to "punch" an opening. Pressure is maintained on the instrument until the "plug" has been removed in order to avoid leaving any residue in the aorta which could constitute an embolus. The side of the fixed blade which opposes the circular cutter is hollow ground to facilitate the cutting action. Formation of an ideal opening, especially since the presence of adventitia in the area readily binds the cutting mechanism, demands a razor-like cutting edge and a very close tolerance between the two shearing edges. Even though the instrument is manufactured as a precision instrument, significant force is required to operate the instrument and blade life is exceedingly short.

SUMMARY OF THE INVENTION

It is an object of the present invention to provide a surgical punch which overcomes the above described disadvantages of prior punches. In accordance with one form of the present invention, an elongated, hollow support sleeve has an elongated rod slidably mounted therein which selectively extends out an open end of said hollow support sleeve. A fixed cutter blade is attached to one end of the support sleeve with the elongated rod passing therethrough and having a mating cutter blade fixedly attached to the end thereof. The mating cutter blade has a diameter smaller than the fixed cutting blade whereby it can be pulled thereinto to give a shearing, cutting action. A handle is attached to the sliding rod and passes through predeterminately shaped guide slots on the elongated, hollow support sleeve whereby the handle can actuate the rod to pull the removable cutter blade into the fixed cutter blade to cut a predetermined shaped opening in tissue. The predeterminately shaped slots include a portion which is circumferentially oriented so that the sliding rod exhibits a rotating action as the handle is pulled to actuate the cutting blades. Rotation of the rod results in rotation of the cutting blades with respect to each other to effect a slicing action rather than a straight punching action of the cutting blades. This allows the blades to cut easier, cleaner, and to last longer. The blades may be specially shaped and the rod may be spring loaded and the entire apparatus provides for ease in disassembly, cleaning, and disinfecting for reuse.

BRIEF DESCRIPTION OF THE DRAWINGS

For a better understanding of the present invention, reference may be had to the following detailed description taken in conjunction with the accompanying drawings in which:

FIG. 4 is a perspective view of a surgical punch in accordance with the present invention; and FIG. 5 is a partial view of the reduced diameter portion of the sleeve of the punch of FIG. 4 illustrating a guide slot for effecting rotational motion of the cutting blades.

DETAILED DESCRIPTION OF THE PREFERRED EMBODIMENT

Figure 1:
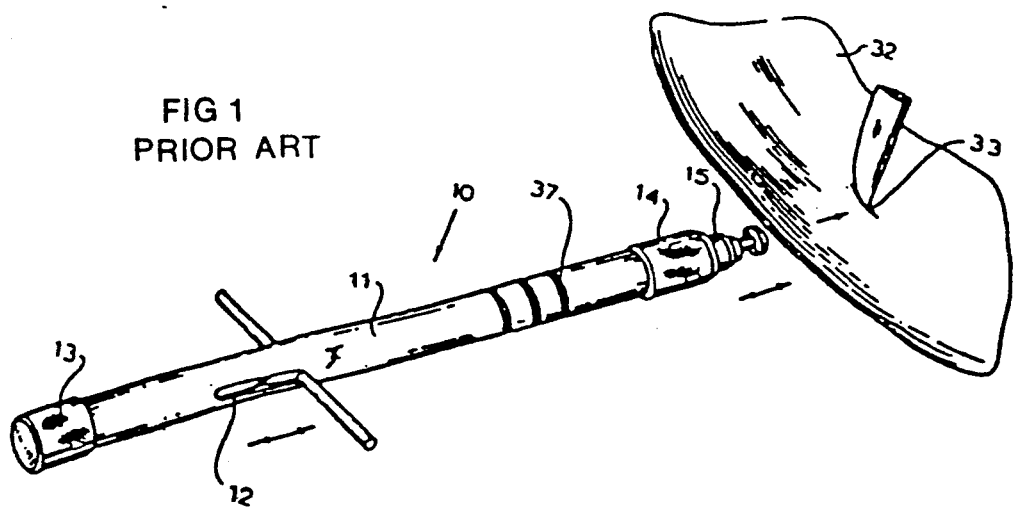
FIG. 1 is a perspective view of an aorta punch of the prior art.
Figure 2:
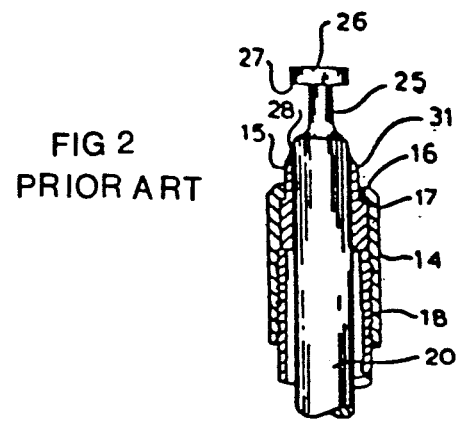
FIG. 2 is a sectional view of the punch of FIG. 1.
Figure 3:
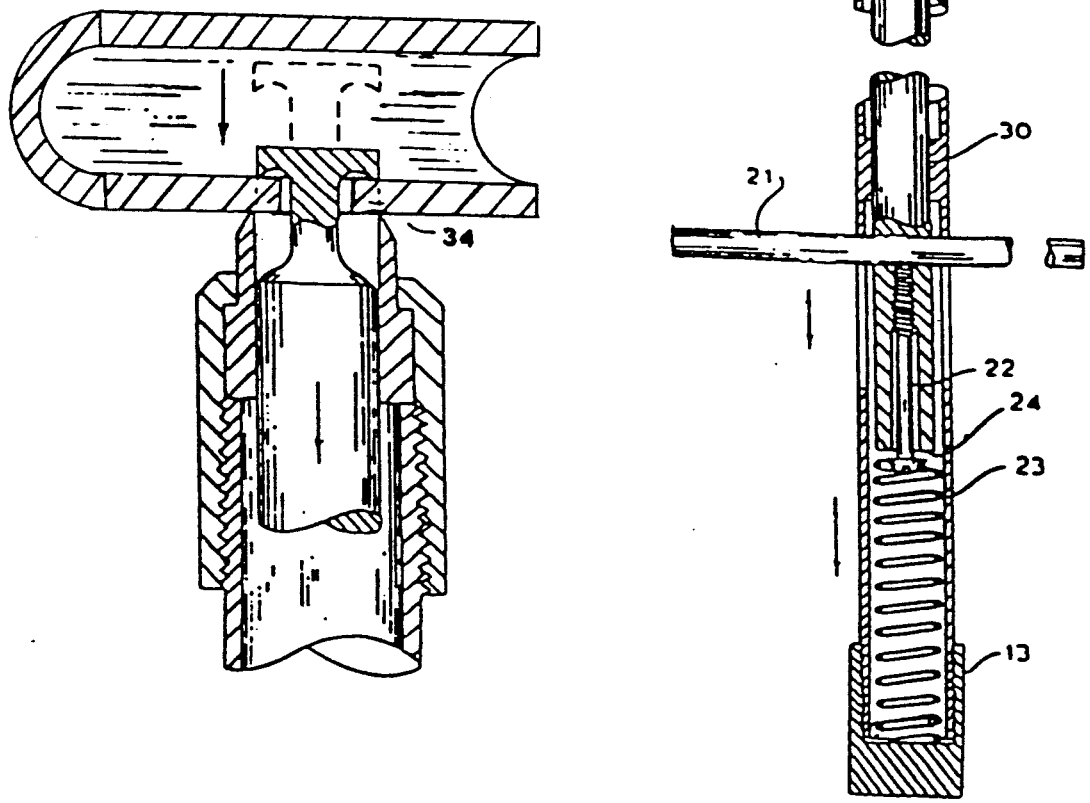
FIG. 3 is a sectional view of the cutting blades and a cardiac section showing the operation of the blades.

Referring now to the drawings and especially to FIGS. 1-3, there is illustrated a surgical punch 10 of the prior art as shown in the aforementioned U.S. Pat. No. 4,018,228 having an elongated, cylindrical tube or sleeve 11, with a pair of slots 12 cut therein along with a knurled and threaded cap 13 at one end and a knurled and threaded blade locking cap 14 at the other end for holding a cylindrical, hollow blade 15 onto the end of the sleeve 11. Blade 15 has an annular ledge 16 surrounding the blade 15 which is held by an internal annular ledge 17 in the locking member 14 which is threaded with threads 18 to the sleeve 1. An internal sliding rod 20 is located inside of the sleeve 1 and has a handle 21 passing therethrough and through slots 12 of the sleeve 11. Handle 21 is attached to rod 20 by means of a threaded screw 22 and is spring biased towards the blade end by a spring 23 held in place by the end cap 13. The spring 23 pushes against the blunt end 24 of rod 20. Rod 20 has a narrowed portion 25 formed in one end thereof which holds a movable fixedly attached blade 26 having a cutting edge 27. Blade 26 is of a slightly smaller diameter than blade 15 so that blade 26 which is generally disc-shaped will slide inside the hollow blade 15 with a close fit to perform a shearing action between the blades 15 and 26. Cutting edge 27 of blade 26 works in connection with the cutting edge 28 of the blade 15 which has been angled inwardly and may be hollow ground to provide a sharp cutting action between the blades as the blade 26 is slid into the blade 15. Blade 26 is actuated by pulling the handle 21 which slides the rod 20 which rides on a raised, annular portion 30 located inside the sleeve 11 and also rides on the internal surface 31 of the blade 15.

The surgical instrument in accordance with FIGS. 1-3 is designed primarily for use in implanting a coronary graft such as an aorta coronary bypass which is accomplished by the grafting of a saphenous vein between the ascending aorta 32 by a small cut 33 with the other end of the saphenous vein attached to a coronary artery. The disc-shaped movable blade 26 is inserted through the cut 33 as illustrated in FIG. 3 with the narrowed portion 25 passing therethrough. Pulling of the handle 21 to slide the rod 20 in the sleeve 11 pulls the blade 26 to shear a circular plug 34 from the aorta wall by the cutting action of the blades 26 and 15 The saphenous vein may then be attached over the opening created by the removal of the punched hole.

The basic elements of FIGS. 1-3 are incorporated in a finished surgical punch having the general appearance shown in FIG. 4. The handle 21 is equivalent to pin 39 and is encompassed within a finger pull 40 which slides on a reduced diameter portion 42 of sleeve 11. The pull 40 has a pair of oppositely extending grips 44 conveniently located to be engaged by index and middle fingers of a person's hand with a thumb or palm of the hand on the end cap 46. Other than the ornamental appearance of the punch of FIG. 4, the primary differences from the punch of FIGS. 1-3 are that the end cap 46 is free to rotate on the sleeve portion 42 and the sleeve 11 rotates with respect to the rod 20.

Turning to FIG. 5, the sleeve portion 42 includes a slot 48 which has an extent thereof proceeding circumferentially about the sleeve. As the pin 39 moves axially of the sleeve 11, it follows the slot 48 and rotates about an axis 50 of the sleeve. Since the pin 39 fits snugly within an aperture passing through rod 20, rotation of pin 39 also causes rotation of rod 20 with respect to sleeve 11. Accordingly, the cutting blade 15 rotates with respect to cutting blade 26 thereby creating a slicing action during operation of the surgical punch. While only the slot 48 is shown, it will be appreciated that pin 39 extends fully through sleeve 11 and that a matching slot to slot 48 is located on the opposing surface of sleeve 11.

The end cap 46 may be rotatably attached to the sleeve 11 in various ways well known in the art. For example, the cap 46 may have a portion extending into the hollow sleeve 11 for maintaining spring 23 in compression against rod 20 and such extending portion may be captured in a circumferential tongue and groove arrangement to allow circumferential rotation. Alternatively, the top member 46A of cap 46 may be attached for rotation with respect to cap 46.

While the principles of the invention have now been made clear in an illustrative embodiment, it will become apparent to those skilled in the art that many modifications of the structures, arrangements, and components presented in the above illustrations may be made in the practice of the invention in order to develop alternate embodiments suitable to specific operating requirements without departing from the spirit and scope of the invention as set forth in the claims which follow.

What is claimed is:

1. A surgical punch apparatus comprising:
   an elongated hollow sleeve;
   an annular cutting blade attached to one end of said sleeve and having an axial passage therethrough;
   an elongated rod slidably movable in said sleeve;
   a movable cutting blade attached to one end of said rod and having an annular cutting edge shaped to slide within said axial passage in said an annular cutting blade whereby said movable cutting blade can be pulled through said annular cutting blade to cut material captured therebetween; and
   means coupling said rod to said sleeve such that axial motion of said rod within said sleeve to effect a cutting action simultaneously effects rotational motion of said rod with respect to said sleeve whereby said cutting action has a slicing component, said coupling means comprising a slot formed in said sleeve and generally axially aligned therewith, a pin extending through said slot and into said rod, said slot having a circumferential portion whereby axial motion of said rod within said sleeve causes said pin to follow said slot and effect a rotation of said rod.

2. The surgical punch apparatus of claim 1 and including an end cap mounted on another end of said sleeve opposite said one end, said end cap being free to rotate circumferentially about said sleeve.

3. The surgical punch apparatus of claim 2 wherein said slot has a first axial portion at one end portion thereof, a second axial portion at another end portion thereof and an intermediate portion extending at least generally circumferentially between said end portions.

* * * * *